(12) United States Patent
Chadeayne (10) Patent No.: US 12,134,598 B2
(45) Date of Patent: Nov. 5, 2024

(54) CRYSTALLINE 5-METHOXY-DIPROPYL TRYPTAMINE COMPOUNDS

(71) Applicant: CAAMTECH, INC., Issaquah, WA (US)

(72) Inventor: Andrew R Chadeayne, Issaquah, WA (US)

(73) Assignee: CAAMTECH, INC., Issaquah, WA (US)

( * ) Notice: Subject to any disclaimer, the term of this patent is extended or adjusted under 35 U.S.C. 154(b) by 0 days.

(21) Appl. No.: 18/264,538

(22) PCT Filed: Jan. 25, 2022

(86) PCT No.: PCT/US2022/013622
§ 371 (c)(1),
(2) Date: Aug. 7, 2023

(87) PCT Pub. No.: WO2022/173584
PCT Pub. Date: Aug. 18, 2022

(65) Prior Publication Data
US 2024/0043381 A1 Feb. 8, 2024

Related U.S. Application Data

(60) Provisional application No. 63/147,355, filed on Feb. 9, 2021.

(51) Int. Cl.
*C07D 209/16* (2006.01)
(52) U.S. Cl.
CPC ........ *C07D 209/16* (2013.01); *C07B 2200/13* (2013.01)
(58) Field of Classification Search
CPC .................. C07D 209/16; A61K 31/4045
See application file for complete search history.

(56) References Cited

U.S. PATENT DOCUMENTS

| | | | |
|---|---|---|---|
| 2018/0021326 A1 | 1/2018 | Stamets | |
| 2018/0221396 A1 | 8/2018 | Chadeayne | |
| 2019/0142851 A1 | 5/2019 | Chadeayne | |
| 2021/0069170 A1* | 3/2021 | Stamets | A61K 31/192 |
| 2021/0300870 A1 | 9/2021 | Chadeayne | |

OTHER PUBLICATIONS

International Search Report and Written Opinion in International Application No. PCT/US2022/013622 dated Apr. 7, 2022.
"Pubchem CID 14011047" Create Date: Feb. 9, 2007, p. 2 formula.
Dolomanov et al., (2009) "OLEX2: A complete structure solution, refinement and analysis program," J. Appl. Cryst. 42, 339-341.
Sheldrick, (2015) "Crystal structure refinement with SHELXL," Acta Cryst., C71, 3-8.
Sheldrick, (2015) "SHELXT—Integrated space-group and crystal structure determination," Acta Cryst., A71, 3-8.
Etter et al., (1990). "Graph-set analysis of hydrogen-bond patterns in organic crystals,"Acta Cryst., B46, 256-262.
Carhart-Harris et al., (2017) "The Therapeutic Potential of Psychedelic Drugs: Past, Present, and Future," Neuropsychopharmacol., 42, 2105-2113.
Chadeayne et al., (2019) "Bis(4-acetoxy-N,N-dimethyltryptammonium) fumarate: a new crystalline form of psilacetin, an alternative to psilocybin as a psilocin prodrug," Acta Cryst., E75, 900-902.
Chadeayne et al., (2019) "N-Methyl-N-propyltryptamine (MPT)," IUCrData, 4, 7, x190962.
Chadeayne et al., (2019) "The Crystal Structure of 4-AcO-DMT Fumarate," Psychedel. Sci. Rev., https://psychedelicreview.com/the-crystal-structure-of-4-aco-dmt-fumarate/.
Chadeayne et al., (2019) "The fumarate salts of the N-isopropyl-N-methyl derivatives of DMT and psilocin," Acta Cryst. (2019). E75, 1316-1320.
Westrip, (2010) "publCIF: software for editing, validating and formatting crystallographic information files," J. Appl. Cryst. 43, 920-925.
International Preliminary Report on Patentability in International Application No. PCT/US2022/013622 dated Aug. 15, 2023.
Falkenberg, (1972) "The Crystal and Molecular Structure of (N,N)-Dimethyltryptamine," Acta Cryst. B28, 3075-3083.
Petcher et al., (1974) "Crystal structures of the Teonanácatl hallucinogens. Part II. Psilocin, C12H15N2O," J. Chem. Soc., Perkin Trans., 2, 946-948.
Weber et al., (1974) "Crystal structures of the Teonanácatl hallucinogens. Part I. Psilocybin C12H17N2O4P," J. Chem. Soc., Perkin Trans., 2, 942-946.
Glennon, R. A. et al., "Serotonin Receptor Binding Affinities of Tryptamine Analogues," Journal of Medicinal Chemistry, 1979, vol. 22, pp. 428-432.
Jefferson S. J. et al. Neuropsychopharmacology (2023) 48:1257-1266; doi.org/10.1038/s41386-023-01572-w.
Ly C. et al. Cell Rep. Jun. 12, 2018; 23(11): 3170-3182. doi:10.1016/j.celrep.2018.05.022.

* cited by examiner

*Primary Examiner* — Deepak R Rao
(74) *Attorney, Agent, or Firm* — RAPHAEL BELLUM PLLC (57) ABSTRACT

The disclosure relates to crystalline form 1 of [2-(5-methoxy-1H-indol-3-yl)ethyl]dipropylamine (5-MeO-DPT) and to crystalline form 1 of bis([2-(5-methoxy-1H-indol-3-yl)ethyl]dipropylazanium) (2E)-but-2-enedioate (5-MeO-DPT fumarate), and to pharmaceutical compositions containing the compounds and methods of treatment using them.

18 Claims, 5 Drawing Sheets

CRYSTALLINE 5-METHOXY-DIPROPYL TRYPTAMINE COMPOUNDS

CROSS-REFERENCE TO RELATED APPLICATIONS

This application claims priority to U.S. Provisional Application No. 63/147,355, filed on Feb. 9, 2021, the disclosure of which is incorporated by reference.

TECHNICAL FIELD

This disclosure relates to crystalline form 1 of [2-(5-methoxy-1H-indol-3-yl)ethyl]dipropylamine (5-MeO-DPT) and to crystalline form 1 of bis([2-(5-methoxy-1H-indol-3-yl)ethyl]dipropylazanium) (2E)-but-2-enedioate (5-MeO-DPT fumarate). This disclosure also relates to pharmaceutical compositions containing the compounds and methods of treatment using them.

BACKGROUND

[2-(5-methoxy-1H-indol-3-yl)ethyl]dipropylamine, or 5-MeO-DPT, is a derivative of psilocin, which is the primary active psychedelic in "magic" mushrooms. Psilocin is the metabolite of psilocybin and its synthetic analogue psilacetin, is a serotonin-2a agonist which results in its mood-altering effects. Tryptamines, both naturally occurring Psilocybin (Weber & Petcher, 1974), Psilocin (Petcher & Weber, 1974), and DMT (Falkenberg, 1972)] and their synthetic derivatives Psilacetin (Chadeayne et al. 2019a, b), MPT (Chadeayne et al. 2019c), MiPT, and 4-HO-MiPT (Chadeayne, Pham et al. 2019)] have garnered a great deal of interest because of their potential to treat depression and post-traumatic stress disorder (PTSD) (Carhart-Harris & Goodwin, 2017). The solid-state structures of bioactive tryptamine molecules are significant because they define each molecule's physical identity, thereby providing the foundation for all downstream research. For example, such fundamental structural characterization is essential for understanding each molecule's biological and clinical properties via structure-activity relationships.

Although therapeutic efficacy is the primary concern for an active pharmaceutical ingredient (API), the salt and solid-state form (i.e., the crystalline or amorphous form) of a drug candidate can be critical to its pharmacological properties, such as bioavailability, and to its development as a viable API. Recently, crystalline forms of API's have been used to alter the physicochemical properties of an API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates (important factors in determining bioavailability). Because these practical physical properties are influenced by the solid-state properties of the crystalline form of the API, they can significantly impact the selection of a compound as an API, the ultimate pharmaceutical dosage form, the optimization of manufacturing processes, and absorption in the body. Moreover, finding the most adequate solid-state form for further drug development can reduce the time and the cost of that development.

Obtaining crystalline forms of an API is extremely useful in drug development. It permits better characterization of the drug candidate's chemical and physical properties. Crystalline forms often have better chemical and physical properties than the API in its amorphous state. Such crystalline forms may possess more favorable pharmaceutical and pharmacological properties or be easier to process.

SUMMARY

The disclosure relates to crystalline form 1 of [2-(5-methoxy-1H-indol-3-yl)ethyl]dipropylamine (5-MeO-DPT) and to crystalline form 1 of bis([2-(5-methoxy-1H-indol-3-yl)ethyl]dipropylazanium) (2E)-but-2-enedioate (5-MeO-DPT fumarate).

Crystalline form 1 of 5-MeO-DPT may be characterized by at least one of: a monoclinic, $P2_1/n$ crystal system space group at a temperature of about 297 K, unit cell dimensions a=6.2223 (3) Å, b=13.0931 (6) Å, c=19.7791 (10) Å, and $\beta$=91.825 (2)°, or an XRPD having peaks at 8.1, 8.9, and 11.2°2θ±0.2°2θ.

Crystalline form 1 of 5-MeO-DPT fumarate may be characterized by at least one of: a triclinic, $P^{-}1$ crystal system space group at a temperature of about 297 K, unit cell dimensions a=9.2956 (6) Å, b=9.4443 (6) Å, c=12.7427 (8) Å, $\alpha$=78.552 (2)°, $\beta$=75.929 (2)°, and $\gamma$=60.806 (2)°, or an XRPD having peaks at 7.2, 13.5, and 14.2°2θ±0.2°2θ.

The disclosure also relates to compositions comprising crystalline form 1 of 5-MeO-DPT or crystalline form 1 of 5-MeO-DPT fumarate. The disclosure further relates to pharmaceutical compositions containing a therapeutically effective amount of crystalline form 1 of 5-MeO-DPT or of crystalline form 1 of 5-MeO-DPT fumarate and an excipient. In one embodiment the excipient is a pharmaceutically acceptable excipient. The disclosure also relates to pharmaceutical compositions comprising a therapeutically effective amount of crystalline form 1 of 5-MeO-DPT or crystalline form 1 of 5-MeO-DPT fumarate and an excipient, wherein the excipient is a pharmaceutically acceptable carrier.

The disclosure also relates to compositions comprising a combination of, as a first component, crystalline form 1 of 5-MeO-DPT or crystalline form 1 of 5-MeO-DPT fumarate and a second component selected from (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone; and a pharmaceutically acceptable excipient.

The disclosure further relates to a method of preventing or treating a psychological disorder comprising the step of administering to a subject in need thereof a therapeutically effective amount of crystalline form 1 of 5-MeO-DPT or crystalline form 1 of 5-MeO-DPT fumarate, or of a pharmaceutical composition containing crystalline form 1 of 5-MeO-DPT or crystalline form 1 of 5-MeO-DPT fumarate.

The disclosure further relates to methods of preventing or treating a physical and/or psychological disorder comprising the step of administering to a subject in need thereof an effective amount of crystalline form 1 of 5-MeO-DPT or of crystalline form 1 of 5-MeO-DPT fumarate and to administering to a subject in need thereof a pharmaceutical composition containing a therapeutically effective amount of crystalline form 1 of 5-MeO-DPT or of crystalline form 1 of 5-MeO-DPT fumarate or a composition according to the disclosure.

The disclosure also relates to methods of preventing or treating inflammation and/or pain comprising the step of administering to a subject in need thereof an effective amount of crystalline form 1 of 5-MeO-DPT or of crystalline form 1 of 5-MeO-DPT fumarate and to administering to a subject in need thereof a pharmaceutical composition containing a therapeutically effective amount of crystalline form 1 of 5-MeO-DPT or of crystalline form 1 of 5-MeO-DPT fumarate or a composition according to the disclosure.

The disclosure also relates to methods of preventing or treating inflammation and/or pain, preventing or treating a neurological disorder, modulating activity of a mitogen activating protein (MAP), modulating neurogenesis, or modulating neurite outgrowth comprising the step of administering to a subject in need thereof a therapeutically effective amount of crystalline form 1 of 5-MeO-DPT or crystalline form 1 of 5-MeO-DPT fumarate, and to administering a pharmaceutical composition or a composition according to the disclosure.

The disclosure also relates to methods of preventing or treating sexual health disorders including, but not limited to, hypoactive sexual desire disorder, hyperactive sexual desire disorder, orgasmic disorder, arousal disorder, vaginismus, and dyspareunia. In some embodiments, the disorder is a male sexual dysfunction disorder. In some embodiments, the disorder is a female sexual dysfunction disorder.

The disclosure also relates to methods of preventing or treating women's health disorders including, but not limited to, menstrual cramping, dysmenorrhea, post-hysterectomic pain, vaginal or vulvar vestibule mucosa disorder, vaginal atrophy, or vulvar vestibulitis.

As used herein, the term "a subject in need thereof" refers a person requiring a composition to treat a particular disease or condition (e.g., inflammation, pain, a psychological disorder, modulating activity at a receptor, etc.). In one embodiment, the "subject in need thereof" may be identified by analyzing, diagnosing, and/or determining whether the person (or subject) requires the composition for treatment of a particular disease or condition. In one embodiment, identifying a person in need of treatment comprises diagnosing a person with a medical condition, e.g., a neurological disorder, a chemical imbalance, a hereditary condition, etc. In one embodiment, identifying a person in need of treatment comprises performing a psychiatric evaluation. In one embodiment, identifying a person in need of treatment comprises performing a blood test. In one embodiment, identifying a person in need of treatment comprises determining whether a person has a compulsive disorder. In one embodiment, identifying a person in need of treatment comprises self-identifying as having a compulsive disorder.

DETAILED DESCRIPTION

This disclosure relates to crystalline form 1 of [2-(5-methoxy-1H-indol-3-yl)ethyl]dipropylamine (5-MeO-DPT) and to crystalline form 1 of bis([2-(5-methoxy-1H-indol-3-yl)ethyl]dipropylazanium) (2E)-but-2-enedioate (5-MeO-DPT fumarate), and to compositions, including pharmaceutical compositions, containing crystalline form 1 of 5-MeO-DPT or crystalline form 1 of 5-MeO-DPT fumarate. The therapeutic uses of crystalline form 1 of 5-MeO-DPT or of crystalline form 1 of 5-MeO-DPT fumarate are described below as well as compositions containing them. The preparation of crystalline form 1 of 5-MeO-DPT or of crystalline form 1 of 5-MeO-DPT fumarate and the methods used to characterize them are described below. The novel and crystalline form 1 of 5-MeO-DPT and crystalline form 1 of 5-MeO-DPT fumarate compounds of the disclosure may be used to prepare other salts, including pharmaceutically acceptable salts, by anion exchange techniques known in the art to exchange the fumarate anion for another desired anion. Crystalline form 1 of 5-MeO-DPT and crystalline form 1 of 5-MeO-DPT fumarate and the methods used to characterize them are described in the examples below.

5-MeO-DPT is a compound of formula (I):

5-MeO-DPT fumarate is a compound of formula (II):

Methods of Treatment and Therapeutic Uses

One embodiment relates to crystalline form 1 of 5-MeO-DPT or to crystalline form 1 of 5-MeO-DPT fumarate and the methods and the compositions—particularly the pharmaceutical compositions—using them to regulate the activity of a neurotransmitter receptor by administering a therapeutically effective dose of crystalline form 1 of 5-MeO-DPT or of crystalline form 1 of 5-MeO-DPT fumarate. Another embodiment relates to crystalline form 1 of 5-MeO-DPT and to crystalline form 1 of 5-MeO-DPT fumarate compounds, according to the disclosure, and the methods and the compositions—particularly the pharmaceutical compositions—of the disclosure are used to treat inflammation and/or pain by administering a therapeutically effective dose of crystalline form 1 of 5-MeO-DPT or of crystalline form 1 of 5-MeO-DPT fumarate.

Methods of the disclosure administer a therapeutically effective amount of crystalline form 1 of 5-MeO-DPT or of crystalline form 1 of 5-MeO-DPT fumarate to prevent or treat a disease or condition, such as those discussed below for a subject in need of treatment. Crystalline form 1 of 5-MeO-DPT or crystalline form 1 of 5-MeO-DPT fumarate may be administered neat or as a composition comprising crystalline form 1 of 5-MeO-DPT or crystalline form 1 of 5-MeO-DPT fumarate as discussed below.

Crystalline form 1 of 5-MeO-DPT or crystalline form 1 of 5-MeO-DPT fumarate may be used to prevent and/or treat a psychological disorder. The disclosure provides a method for preventing and/or treating a psychological disorder by administering to a subject in need thereof a therapeutically effective amount of crystalline form 1 of 5-MeO-DPT or of crystalline form 1 of 5-MeO-DPT fumarate. The psychological disorder may be chosen from depression, psychotic disorder, schizophrenia, schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome; post-traumatic stress disorder (PTSD); premenstrual dysphoric disorder (PMDD); and premenstrual syndrome (PMS).

Crystalline form 1 of 5-MeO-DPT or crystalline form 1 of 5-MeO-DPT fumarate may be used to prevent and/or treat a brain disorder. The disclosure provides a method for preventing and/or treating a brain disorder by administering to a subject in need thereof a therapeutically effective amount of crystalline form 1 of 5-MeO-DPT or of crystalline form 1 of 5-MeO-DPT fumarate. The brain disorder is chosen from Huntington's disease, Alzheimer's disease, dementia, and Parkinson's disease.

Crystalline form 1 of 5-MeO-DPT or crystalline form 1 of 5-MeO-DPT fumarate may also be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of crystalline form 1 of 5-MeO-DPT or of crystalline form 1 of 5-MeO-DPT fumarate.

Crystalline form 1 of 5-MeO-DPT or crystalline form 1 of 5-MeO-DPT fumarate may be used to prevent and/or treat inflammation and/or pain, such as for example inflammation and/or pain associated with inflammatory skeletal or muscular diseases or conditions. The disclosure provides a method for preventing and/or treating an inflammation and/or pain by administering to a subject in need thereof a therapeutically effective amount of crystalline form 1 of 5-MeO-DPT or of crystalline form 1 of 5-MeO-DPT fumarate. Generally speaking, treatable "pain" includes nociceptive, neuropathic, and mix-type. A method of the disclosure may reduce or alleviate the symptoms associated with inflammation, including but not limited to treating localized manifestation of inflammation characterized by acute or chronic swelling, pain, redness, increased temperature, or loss of function in some cases. A method of the disclosure may reduce or alleviate the symptoms of pain regardless of the cause of the pain, including but not limited to reducing pain of varying severity, i.e., mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include but are not limited to musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

Crystalline form 1 of 5-MeO-DPT or crystalline form 1 of 5-MeO-DPT fumarate may be used to modulate activity of a mitogen activating protein (MAP), comprising administering a composition of the invention. In one embodiment, the mitogen activating protein (MAP) comprises a MAP kinase (MAPk). MAPKs provide a wide-ranging signaling cascade that allow cells to quickly respond to biotic and abiotic stimuli. Exemplary MAPKs include, but are not limited to, Tropomyosin Receptor Kinase A (TrkA), P38-alpha, Janus Kinase 1 (JAK1), and c-Jun N-Terminal Kinase 3 (JNK3). TrkA is a high affinity catalytic receptor of nerve growth factor (NGF) protein. TrkA regulates NGF response, influencing neuronal differentiation and outgrowth as well as programmed cell death. p38-alpha is involved with the regulation of pro-inflammatory cytokines, including TNF-$\alpha$. In the central nervous system, p38-alpha regulates neuronal death and neurite degeneration, and it is a common target of Alzheimer's disease therapies. JAK1 influences cytokine signaling, including IL-2, IL-4, IFN-alpha/beta, IFN-$\gamma$, and IL-10, and it is implicated in brain aging. JNK3 is neuronal specific protein isoform of the JNKs. It is involved with the regulation of apoptosis. JNK3 also plays a role in modulating the response of cytokines, growth factors, and oxidative stress.

As used herein, the term "modulating activity of a mitogen activating protein" refers to changing, manipulating, and/or adjusting the activity of a mitogen activating protein. In one embodiment, modulating the activity of a MAP, such as a MAPK, can influence neural health, neurogenesis, neural growth and differentiation, and neurodegenerative diseases.

Crystalline form 1 of 5-MeO-DPT or crystalline form 1 of 5-MeO-DPT fumarate may be used to modulate neurogenesis, comprising administering a composition of the invention. As used herein, the term "modulating neurite outgrowth" refers to changing, manipulating, and/or adjusting the growth and development of neural projections, or "neurites." In one embodiment, neurogenesis comprises modulating the growth of new neurites, the number of neurites per neuron, and/or neurite length. In one embodiment, modulating neurite outgrowth comprises increasing and/or enhancing the rate and/or length at which neurites develop.

Crystalline form 1 of 5-MeO-DPT or crystalline form 1 of 5-MeO-DPT fumarate may be used to modulate neurite outgrowth, comprising administering a composition of the invention. As used herein, the term "modulating neurogenesis" refers to changing, manipulating, and/or adjusting the growth and development of neural tissue. In one embodiment, neurogenesis comprises adult neurogenesis, in which new neural stem cells are generated from neural stem cells in an adult animal. In one embodiment, modulating neurogenesis comprises increasing and/or enhancing the rate at which new neural tissue is developed.

The disclosure also relates to methods of preventing or treating sexual health disorders including, but not limited to, hypoactive sexual desire disorder, hyperactive sexual desire disorder, orgasmic disorder, arousal disorder, vaginismus, and dyspareunia. In some embodiments, the disorder is a male sexual dysfunction disorder. In some embodiments, the disorder is a female sexual dysfunction disorder.

The disclosure also relates to methods of preventing or treating women's health disorders including, but not limited to, menstrual cramping, dysmenorrhea, post-hysterectomic pain, vaginal or vulvar vestibule mucosa disorder, vaginal atrophy, or vulvar vestibulitis.

Compositions

The disclosure also relates to compositions comprising an effective amount of crystalline form 1 of 5-MeO-DPT or of crystalline form 1 of 5-MeO-DPT fumarate, and an excipient (e.g., a pharmaceutically-acceptable excipient). In another embodiment, the disclosure also relates to pharmaceutical compositions comprising a therapeutically effective amount of crystalline form 1 of 5-MeO-DPT or of crystalline form 1 of 5-MeO-DPT fumarate and a pharmaceutically acceptable carrier (also known as a pharmaceutically acceptable excipient). As discussed above, crystalline form 1 of 5-MeO-DPT or crystalline form 1 of 5-MeO-DPT fumarate may be, for example, therapeutically useful to prevent and/or treat the psychological and other disorders discussed above.

A composition or a pharmaceutical composition of the disclosure may be in any form which contains crystalline form 1 of 5-MeO-DPT or crystalline form 1 of 5-MeO-DPT fumarate. The composition may be, for example, a tablet, capsule, liquid suspension, injectable, topical, or transdermal. The compositions or pharmaceutical compositions generally contain, for example, about 1% to about 99% by weight of crystalline form 1 of 5-MeO-DPT or of crystalline form 1 of 5-MeO-DPT fumarate and, for example, 99% to 1% by weight of at least one suitable pharmaceutical excipient. In one embodiment, the composition may be between about 5% and about 75% by weight of crystalline form 1 of 5-MeO-DPT or of crystalline form 1 of 5-MeO-DPT fumarate with the rest being at least one suitable pharmaceutical excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, crystalline form 1 of 5-MeO-DPT or crystalline form 1 of 5-MeO-DPT fumarate may be used as the "first purified psilocybin derivative" in the compositions described in US 2018/0221396 A1 and US 2019/0142851 A1. Accordingly, this disclosure provides a composition comprising as a first component: crystalline form 1 of 5-MeO-DPT or crystalline form 1 of 5-MeO-DPT fumarate; and as a second component selected from (a) a serotonergic drug, (b) a purified psilocybin derivative, (c) one or two purified cannabinoids and (d) a purified terpene; with the rest being at least one suitable pharmaceutical excipient or at least one other adjuvant, as discussed below. Such a composition may be a pharmaceutical composition wherein the components are present individually in therapeutic effective amounts or by combination in a therapeutically effective amount to treat a disease, disorder, or condition as described herein.

When used in such compositions as a first component comprising crystalline form 1 of 5-MeO-DPT or crystalline form 1 of 5-MeO-DPT fumarate of the disclosure with a second component selected from at least one of (a) a serotonergic drug, (b) a purified psilocybin derivative, (c) a purified cannabinoid, or (d) a purified terpene, the compositions represent particular embodiments of the invention. Compositions having as a first component crystalline form 1 of 5-MeO-DPT or crystalline form 1 of 5-MeO-DPT fumarate of the disclosure with a second component selected from at least one of (e) an adrenergic drug, (f) a dopaminergic drug, (g) a monoamine oxidase inhibitor, (h) a purified erinacine, (i) a purified hericenone represent additional particular embodiments of the invention represented by the compositions having crystalline form 1 of 5-MeO-DPT or crystalline form 1 of 5-MeO-DPT fumarate according to the disclosure. In some embodiments, the first and second components can be administered at the same time (e.g., together in the same composition), or at separate times over the course of treating a patient in need thereof. Such a composition may be a pharmaceutical composition wherein the components are present individually in therapeutically effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed preferred embodiments, incorporated here by reference. Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed preferred embodiments. Exemplary cannabinoids include but are not limited to the cannabinoids described in paragraphs [0111]-[0159] of US 2018/0221396 A1 and [0112]-[0160] US 2019/0142851 A1 as well as the disclosed preferred embodiments. Exemplary terpenes include but are not limited to the terpenes described in paragraphs [0160]-[0238] of US 2018/0221396 A1 and [0161]-[0300] US 2019/0142851 A1 as well as the disclosed preferred embodiments.

A pharmaceutical formulation of the disclosure may comprise, consist essentially of, or consist of (a) crystalline form 1 of 5-MeO-DPT or crystalline form 1 of 5-MeO-DPT fumarate of the disclosure and (b) at least one second active compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone and (c) a pharmaceutically acceptable excipient. In some embodiments, crystalline form 1 of 5-MeO-DPT or crystalline form 1 of 5-MeO-DPT fumarate and the second active compound(s) are each present in a therapeutically effective amount using a purposefully engineered and unnaturally occurring molar ratios. Exemplary molar ratios of crystalline form 1 of 5-MeO-DPT or crystalline form 1 of 5-MeO-DPT fumarate of the disclosure to the second active compound in a composition of the disclosure include but are not limited to from about to about 100:0.1, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition containing crystalline form 1 of 5-MeO-DPT or crystalline form 1 of 5-MeO-DPT fumarate of the disclosure and a serotonergic drug, a purified psilocybin derivative, a purified cannabinoid, or a purified terpene, each present in a therapeutically effective amount using a purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. The disclosures of US 2018/0221396 A1 and US 2019/0142851 A1 are incorporated herein by reference. According to this disclosure composition containing crystalline form 1 of 5-MeO-DPT or crystalline form 1 of 5-MeO-DPT fumarate of the disclosure may be used in place of a "purified psilocybin derivative" in the compositions described in US 2018/0221396 A1 and US 2019/0142851 A1. Accordingly, the disclosure provides a pharmaceutical formulation comprising as (a) crystalline form 1 of 5-MeO-DPT or crystalline form 1 of 5-MeO-DPT fumarate of the disclosure and at least one second component selected from (a) a purified psilocybin derivative, (b) a purified cannabinoid or (c) a purified terpene; and at least one pharmaceutically-acceptable excipient or at least one other adjuvant, as described herein. Such a composition may be a pharmaceutical composition wherein the components are present individually in therapeutic effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments, incorporated here by reference. Some exemplary serotonergic drugs include SSRIs and SNRIs. Some examples of specific serotonergic drugs include the following molecules, including any salts, solvates, or polymorphs thereof: 6-Allyl-N,N-diethyl-NL, N,N-Dibutyl-T, N,N-Diethyl-T, N,N-Diisopropyl-T, N,N-Dimethyl-T, 2,alpha-Dimethyl-T, alpha,N-Dimethyl-T, N,N-Dipropyl-T, N-Ethyl-N-isopropyl-T, alpha-Ethyl-T, 6,N,N-Triethyl-NL, 3,4-Dihydro-7-methoxy-1-methyl-C, 7-Methyoxy-1-methyl-C, N,N-Dibutyl-4-hydroxy-T, N,N-Diethyl-4-hydroxy-T, N,N-Diisopropyl-4-hydroxy-T, N,N-Dimethyl-4-hydroxy-T, N,N-Dimethyl-5-hydroxy-T, N,N-Dipropyl-4-hydroxy-T, N-Ethyl-4-hydroxy-N-methyl-T, 4-Hydroxy-N-isopropyl-N-methyl-T, 4-Hydroxy-N-methyl-N-propyl-T, 4-Hydroxy-N,N-tetramethylene-T Ibogaine, N,N-Diethyl-L, N-Butyl-N-methyl-T, N,N-Diisopropyl-4,5-methylenedioxy-T, N,N-Diisopropyl-5,6-methylenedioxy-T, N,N-Dimethyl-4,5-methylenedioxy-T, N,N-Dimethyl-5,6-methylenedioxy-T, N-Isopropyl-N-methyl-5,6-methylenedioxy-T, N,N-Diethyl-2-methyl-T, 2,N,N-Trimethyl-T, N-Acetyl-5-methoxy-T, N,N-Diethyl-5-methoxy-T, N,N-Diisopropyl-5-methoxy-T, 5-Methoxy-N,N-dimethyl-T, N-Isopropyl-4-methoxy-N-methyl-T, N-Isopropyl-5-methoxy-N-methyl-T, 5,6-Dimethoxy-N-isopropyl-N-methyl-T, 5-Methoxy-N-methyl-T, 5-Methoxy-N,N-tetramethylene-T, 6-Methoxy-1-methyl-1,2,3,4-tetrahydro-C, 5-Methoxy-2,N,N-trimethyl-T, N,N-Dimethyl-5-methylthio-T, N-Isopropyl-N-methyl-T, alpha-Methyl-T, N-Ethyl-T, N-Methyl-T, 6-Propyl-N L, N,N-Tetramethylene-T, Tryptamine, and 7-Methoxy-1-methyl-1,2,3,4-tetrahydro-C, alpha,N-Dimethyl-5-methoxy-T. For additional information regarding these compounds see Shulgin, A. T., & Shulgin, A. (2016). Tihkal: The Continuation. Berkeley, Calif.: Transform Press. In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof. In an exemplary embodiment, the serotonergic drug is 3,4-methylenedioxymethamphetamine.

Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed exemplary embodiments, incorporated here by reference. In one embodiment, the compositions disclosed herein comprise one or more purified psilocybin derivatives chosen from: [3-(2-Dimethylaminoethyl)-1H-indol-4-yl] dihydrogen phosphate, 4-hydroxytryptamine, 4-hydroxy-N,N-dimethyltryptamine, [3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, [3-(2-trimethylaminoethyl)-1H-indol-4-yl] dihydrogen phosphate, and 4-hydroxy-N,N,N-trimethyltryptamine.

Exemplary cannabinoids include but are not limited to the cannabinoids described in paragraphs [0111]-[0159] of US 2018/0221396 A1 and [0112]-[0160] US 2019/0142851 A1 as well as the disclosed exemplary embodiments, incorporated here by reference. Examples of cannabinoids within the context of this disclosure include the following molecules: Cannabichromene (CBC), Cannabichromenic acid (CBCA), Cannabichromevarin (CBCV), Cannabichromevarinic acid (CBCVA), Cannabicyclol (CBL), Cannabicyclolic acid (CBLA), Cannabicyclovarin (CBLV), Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoic acid B (CBEA-B), Cannabielsoin (CBE), Cannabielsoin acid A (CBEA-A), Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA), Cannabinodiol (CBND), Cannabinodivarin (CBDV), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriol (CBT), Cannabitriolvarin (CBTV), 10-Ethoxy-9-hydroxy-delta-6a-tetrahydrocannabinol, Cannbicitran (CBT), Cannabiripsol (CBR), 8,9-Dihydroxy-delta-6a-tetrahydrocannabinol, Delta-8-tetrahydrocannabinol (Δ8-THC), Delta-8-tetrahydrocannabinolic acid (A8-THCA), Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), 10-Oxo-delta-6a-tetrahydrocannabinol (OTHC), Cannabichromanon (CBCF), Cannabifuran (CBF), Cannabiglendol, Delta-9-cis-tetrahydrocannabinol (cis-THC), Tryhydroxy-delta-9-tetrahydrocannabinol (triOH-THC), Dehydrocannabifuran (DCBF), and 3,4,5,6-Tetrahydro-7-hydroxy-alpha-alpha-2-trimethyl-9-n-propyl-2,6-metha-no-2H-1-benzoxocin-5-methanol. In one embodiment, the purified cannabinoid is chosen from THC, THCA, THCV, THCVA, CBC, CBCA, CBCV, CBCVA, CBD, CBDA, CBDV, CBDVA, CBG, CBGA, CBGV, or CBGVA.

Exemplary terpenes include but are not limited to the terpenes described in paragraphs [0160]-[0238] of US 2018/0221396 A1 and [0161]-[0300] US 2019/0142851 A1 as well as the disclosed exemplary embodiments, incorporated here by reference. In one embodiment, a purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, caryophyllene, caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin. In one embodiment, a purified terpene is chosen from bornyl acetate, alpha-bisabolol, borneol, camphene, camphor, carene, caryophyllene, cedrene, cymene, elemene, eucalyptol, eudesmol, farnesene, fenchol, geraniol, guaiacol, humulene, isoborneol, limonene, linalool, menthol, myrcene, nerolidol, ocimene, phellandrene, phytol, pinene, pulegone, sabinene, terpineol, terpinolene, or valencene.

As used herein, the term "adrenergic drug" refers to a compound that binds, blocks, or otherwise influences (e.g., via an allosteric reaction) activity at an adrenergic receptor. In one embodiment, an adrenergic drug binds to an adrenergic receptor. In one embodiment, an adrenergic drug indirectly affects an adrenergic receptor, e.g., via interactions affecting the reactivity of other molecules at the adrenergic receptor. In one embodiment, an adrenergic drug is an agonist, e.g., a compound activating an adrenergic receptor. In one embodiment, an adrenergic drug is an antagonist, e.g., a compound binding but not activating an adrenergic receptor, e.g., blocking a receptor. In one embodiment, an adrenergic drug is an effector molecule, e.g., a compound binding to an enzyme for allosteric regulation. In one embodiment, an adrenergic drug acts (either directly or indirectly) at more than one type of receptor (e.g., 5HT, dopamine, adrenergic, acetylcholine, etc.).

In one embodiment, an adrenergic drug is an antidepressant. In one embodiment, an adrenergic drug is a norepinephrine transporter inhibitor. In one embodiment, an adrenergic drug is a vesicular monoamine transporter inhibitor. In one embodiment, an adrenergic drug is chosen from adrenaline, agmatine, amoxapine, aptazapine, atomoxetine, bupropion, clonidine, doxepin, duloxetine, esmirtazpine, mianserin, ketanserin, mirabegron, mirtazapine, norepinephrine, phentolamine, phenylephrine, piperoxan, reserpine, ritodrine, setiptiline, tesofensine, timolol, trazodone, trimipramine, or xylazine.

As used herein, the term "dopaminergic drug" refers to a compound that binds, blocks, or otherwise influences (e.g., via an allosteric reaction) activity at a dopamine receptor. In one embodiment, a dopaminergic drug binds to a dopamine receptor. In one embodiment, a dopaminergic drug indirectly affects a dopamine receptor, e.g., via interactions affecting the reactivity of other molecules at the dopamine receptor. In one embodiment, a dopaminergic drug is an agonist, e.g., a compound activating a dopamine receptor. In one embodiment, a dopaminergic drug is an antagonist, e.g., a compound binding but not activating a dopamine receptor, e.g., blocking a receptor. In one embodiment, a dopaminergic drug is an effector molecule, e.g., a compound binding to an enzyme for allosteric regulation. In one embodiment, a dopaminergic drug acts (either directly or indirectly) at more than one type of receptor (e.g., 5HT, dopamine, adrenergic, acetylcholine, etc.).

In one embodiment, a dopaminergic drug is a dopamine transporter inhibitor. In one embodiment, a dopaminergic drug is a vesicular monoamine transporter inhibitor. In one embodiment, a dopaminergic drug is chosen from amineptine, apomorphine, benzylpiperazine, bromocriptine, cabergoline, chlorpromazine, clozapine, dihydrexidine, domperidone, dopamine, fluphenazine, haloperidol, ketamine, loxapine, methamphetamine, olanzapine, pemoline, perphenazine, pergolide, phencyclidine, phenethylamine, phenmetrazine, pimozide, piribedil, a psychostimulant, reserpine, risperidone, ropinirole, tetrabenazine, or thioridazine.

As used herein, the term "monoamine oxidase inhibitor" (MAOI) refers to a compound that blocks the actions of monoamine oxidase enzymes. In on embodiment, a MAOI inhibits the activity of one or both monoamine oxidase A and monoamine oxidase B. In one embodiment a MAOI is a reversible inhibitors of monoamine oxidase A. In one embodiment a MAOI is a drug chosen from isocarboxazid, phenelzine, or tranylcypromine.

In one embodiment, the compositions and methods disclosed herein include one or more purified erinacine molecules. In one embodiment, the compositions and methods disclosed herein comprise purified erinacine A. In one embodiment, the compositions and methods disclosed herein comprise erinacine B. In one embodiment, the compositions and methods disclosed herein comprise erinacine C. In one embodiment, the compositions and methods disclosed herein comprise erinacine D. In one embodiment, the compositions and methods disclosed herein comprise erinacine E. In one embodiment, the compositions and methods disclosed herein comprise erinacine F. In one embodiment, the compositions and methods disclosed herein comprise erinacine G. In one embodiment, the compositions and methods disclosed herein comprise erinacine H. In one embodiment, the compositions and methods disclosed herein comprise erinacine I. In one embodiment, the compositions and methods disclosed herein comprise erinacine J. In one embodiment, the compositions and methods disclosed herein comprise erinacine K In one embodiment, the compositions and methods disclosed herein comprise erinacine P. In one embodiment, the compositions and methods disclosed herein comprise erinacine Q. In one embodiment, the compositions and methods disclosed herein comprise erinacine R. In one embodiment, the compositions and methods disclosed herein comprise erinacine S.

In one embodiment, the compositions and methods disclosed herein include one or more purified hericenone molecules. In one embodiment, the compositions and methods disclosed herein comprise purified hericenone A. In one embodiment, the compositions and methods disclosed herein comprise purified hericenone B. In one embodiment, the compositions and methods disclosed herein comprise purified hericenone C. In one embodiment, the compositions and methods disclosed herein comprise purified hericenone D. In one embodiment, the compositions and methods disclosed herein comprise purified hericenone E. In one embodiment, the compositions and methods disclosed herein comprise purified hericenone F. In one embodiment, the compositions and methods disclosed herein comprise purified hericenone G. In one embodiment, the compositions and methods disclosed herein comprise purified hericenone H.

Exemplary compositions of crystalline form 1 of 5-MeO-DPT or crystalline form 1 of 5-MeO-DPT fumarate of the disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone in exemplary molar ratios are shown in Table 1. Crystalline form 1 of 5-MeO-DPT or crystalline form 1 of 5-MeO-DPT fumarate of the disclosure may be any one of the exemplary embodiments described above including the crystalline form one of those compounds as disclosed herein.

TABLE 1

| Second Compound | Molar ratio of Crystalline form 1 of 5-MeO-DPT or crystalline form 1 of 5-MeO-DPT fumarate:second compound | Molar ratio of Crystalline form 1 of 5-MeO-DPT or crystalline form 1 of 5-MeO-DPT fumarate:second compound | Molar ratio of a Crystalline form 1 of 5-MeO-DPT or crystalline form 1 of 5-MeO-DPT fumarate:second compound |
| --- | --- | --- | --- |
| 3,4 methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |

TABLE 1-continued

| Second Compound | Molar ratio of Crystalline form 1 of 5-MeO-DPT or crystalline form 1 of 5-MeO-DPT fumarate:second compound | Molar ratio of Crystalline form 1 of 5-MeO-DPT or crystalline form 1 of 5-MeO-DPT fumarate:second compound | Molar ratio of a Crystalline form 1 of 5-MeO-DPT or crystalline form 1 of 5-MeO-DPT fumarate:second compound |
|---|---|---|---|
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

Exemplary pharmaceutical compositions of crystalline form 1 of 5-MeO-DPT or crystalline form 1 of 5-MeO-DPT fumarate of the disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, or a purified hericenone and an excipient with exemplary molar ratios of crystalline form 1 of 5-MeO-DPT or crystalline form 1 of 5-MeO-DPT fumarate to the second compound are shown in Table 2. Crystalline form 1 of 5-MeO-DPT or crystalline form 1 of 5-MeO-DPT fumarate of the disclosure may be any one of the exemplary embodiments described above including the crystalline form one of those compounds as disclosed herein.

TABLE 2

| Second Compound | Molar ratio of a Crystalline form 1 of 5-MeO-DPT or crystalline form 1 of 5-MeO-DPT fumarate:second compound | Molar ratio of a Crystalline form 1 of 5-MeO-DPT or crystalline form 1 of 5-MeO-DPT fumarate:second compound | Molar ratio of a Crystalline form 1 of 5-MeO-DPT or crystalline form 1 of 5-MeO-DPT fumarate:second compound |
|---|---|---|---|
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |

TABLE 2-continued

| Second Compound | Molar ratio of a Crystalline form 1 of 5-MeO-DPT or crystalline form 1 of 5-MeO-DPT fumarate:second compound | Molar ratio of a Crystalline form 1 of 5-MeO-DPT or crystalline form 1 of 5-MeO-DPT fumarate:second compound | Molar ratio of a Crystalline form 1 of 5-MeO-DPT or crystalline form 1 of 5-MeO-DPT fumarate:second compound |
|---|---|---|---|
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |
| Adrenaline | About 1:100 to about 100:1 | About 1:25 to about 25:1 | About 1:5 to about 5:1 |
| Amineptine | About 1:100 to about 100:1 | About 1:25 to about 25:1 | About 1:5 to about 5:1 |
| Erinacine A | About 1:100 to about 100:1 | About 1:25 to about 25:1 | About 1:5 to about 5:1 |
| Hericenone A | About 1:100 to about 100:1 | About 1:25 to about 25:1 | About 1:5 to about 5:1 |
| Phenelzine | About 1:100 to about 100:1 | About 1:25 to about 25:1 | About 1:5 to about 5:1 |

An "effective amount" or a "therapeutically effective amount" of crystalline form 1 of 5-MeO-DPT or of crystalline form 1 of 5-MeO-DPT fumarate is generally in the range of about 0.1 to about 100 mg daily (oral dose), of about 0.1 to about 50 mg daily (oral dose) of about 0.25 to about 25 mg daily (oral dose), of about 0.1 to about 5 mg daily (oral dose) or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. Crystalline form 1 of 5-MeO-DPT or crystalline form 1 of 5-MeO-DPT fumarate according to the disclosure, compositions and pharmaceutical compositions containing it may be used in combination with other agents that are generally administered to a patient being treated for psychological and other disorders discussed above. They may also be co-formulated with one or more of such agents in a single pharmaceutical composition.

Depending on the type of composition or pharmaceutical composition, the excipient or pharmaceutically acceptable carrier may be chosen from any one or a combination of carriers known in the art. The choice of the pharmaceutically acceptable carrier depends upon the pharmaceutical form and the desired method of administration to be used. Preferred carriers include those that do not substantially alter the crystalline form 1 of 5-MeO-DPT or the crystalline form 1 of 5-MeO-DPT fumarate or produce undesirable biological effects or otherwise interact in a deleterious manner with any other component(s) of the pharmaceutical composition.

The compositions or pharmaceutical compositions of the disclosure may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, the crystalline form one of 5-MeO-DPT and crystalline form 1 of 5-MeO-DPT fumarate according to the disclosure may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Excipients or pharmaceutically acceptable adjuvants known in the formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a composition or a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of crystalline form 1 of 5-MeO-DPT or of crystalline form 1 of 5-MeO-DPT fumarate of the disclosure in pure form, with a permeation enhancer, with stabilizers (e.g. antioxidants), or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, liquid dosage forms, such as, for example, tablets, suppositories, pills, soft elastic and hard gelatin capsules, powders, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

EXAMPLES

The preparation of crystalline form 1 of 5-MeO-DPT and of crystalline form 1 of 5-MeO-DPT fumarate, are described below.

Synthesis and Crystallization

A commercial sample (purchased from Chem Logix) of 5-MeO-DPT freebase was slowly evaporated in an acetone solution resulting in the formation of crystals of 5-methoxy-N,N-di-n-propyl-tryptamine suitable for X-ray analysis. Crystals of bis-(5-meth-oxy-N,N-di-n-propyl-tryptammonium) fumarate were grown from the slow evaporation of an aceto-nitrile solution of a commercial sample (purchased from Chem Logix) of 5-MeO-DPT fumarate.

Single crystal data, data collection and structure refinement details are summarized in Table 3. The data for crystalline form 1 of 5-MeO-DPT fumarate in Table 3 relates to the asymmetric unit.

TABLE 3

| | 5-MeO-DPT | 5-MeO-DPT Fumarate |
|---|---|---|
| Chemical formula | $C_{17}H_{26}N_2O$ | $C_{17}H_{27}N_2O \cdot C_2HO_2$ (unit cell) |
| $M_r$ | 274.40 | 332.43 |
| Crystal system, space group | Monoclinic, $P2_1/n$ | Triclinic, $P^-1$ |
| Temperature (K) | 297 | 297 |
| a, b, c (Å) | 6.2223 (3), 13.0931 (6), 19.7791 (10) | 9.2956 (6), 9.4443 (6), 12.7427 (8) |
| α (°) | | 78.552 (2) |
| β (°) | 91.825 (2) | 75.929 (2) |
| γ (°) | | 60.806 (2) |
| V (Å$^3$) | 1610.57 (13) | 943.06 (11) |
| Z | 4 | 2 |
| F(000) | 600 | 360 |
| $D_x$ (Mg m$^{-3}$) | 1.132 | 1.171 |
| Radiation type | $M_o K_\alpha$ | $M_o K_\alpha$ |
| λ (Å) | 0.71073 | 0.71073 |
| μ (mm$^{-1}$) | 0.07 | 0.08 |
| Crystal size (mm) | 0.38 × 0.3 × 0.06 | 0.3 × 0.22 × 0.2 |
| Diffractometer | Bruker D8 CMOS | Bruker D8 CMOS |
| Absorption correction | Multi-scan | Multi-scan |
| | SADABS2016/2 (Bruker, 2016/2) was used for absorption correction. wR2(int) was 0.0624 before and 0.0538 after correction. The Ratio of minimum to maximum transmission is 0.9215. The λ/2 correction factor is not present. | SADABS2016/2 (Bruker, 2016/2) was used for absorption correction. wR2(int) was 0.0528 before and 0.0455 after correction. The Ratio of minimum to maximum transmission is 0.9685. The λ/2 correction factor is not present. |

TABLE 3-continued

| | 5-MeO-DPT | 5-MeO-DPT Fumarate |
|---|---|---|
| $T_{min}$, $T_{max}$ | 0.687, 0.745 | 0.722, 0.745 |
| No. of measured, independent and observed [I > 2s(I)] reflections | 29365, 3035, 2466 | 37231, 3565, 3006 |
| $R_{int}$ | 0.038 | 0.032 |
| $\theta_{max}$, $\theta_{min}$ (°) | 25.7, 3.3 | 25.8, 2.6 |
| $R[F^2 > 2\sigma(F^2)]$, $wR(F^2)$, S | 0.042, 0.117, 1.06 | 0.052, 0.142, 1.05 |
| w | $1/[\sigma^2(F_o^2) + (0.050P)^2 + 0.3694P]$ where $P = (F_o^2 + 2F_c^2)/3$ | $1/[\sigma^2(F_o^2) + (0.0652P)^2 + 0.3068P]$ where $P = (F_o^2 + 2F_c^2)/3$ |
| No. of reflections | 3035 | 3565 |
| No. of parameters | 189 | 228 |
| No. of restraints | 0 | 0 |
| h, k, l | $-7 \rightarrow 7$, $-15 \rightarrow 15$, $-24 \rightarrow 24$ | $-11 \rightarrow 11$, $-11 \rightarrow 11$, $-15 \rightarrow 15$ |
| H-site location | mixed | mixed |
| H-atom treatment | H atoms treated by a mixture of independent and constrained refinement | H atoms treated by a mixture of independent and constrained refinement |
| $(\Delta/\sigma)_{max}$ | <0.001 | <0.001 |
| $\Delta\rangle_{max}$, $\Delta\rangle_{min}$ (e Å$^{-3}$) | 0.14, −0.17 | 0.29, −0.15 |
| Extinction Correction | SHELXL2018 (Sheldrick, 2015b), $Fc^* = kFc[1 + 0.001 \times Fc^2\lambda^3/\sin(2\theta)]^{-1/4}$ | |
| Extinction Coefficient | 0.046 (13) | |

Data collection: APEX3 (Bruker, 2018);
cell refinement: SAINT (Bruker, 2018);
data reduction: SAINT (Bruker, 2018);
program(s) used to solve structure: SHELXT2014 (Sheldrick, 2015a);
program(s) used to refine structure: SHELXL2018 (Sheldrick, 2015b);
molecular graphics: OLEX2 (Dolomanov et al., 2009);
software used to prepare material for publication: publCIF (Westrip, 2010).

Figure 1:
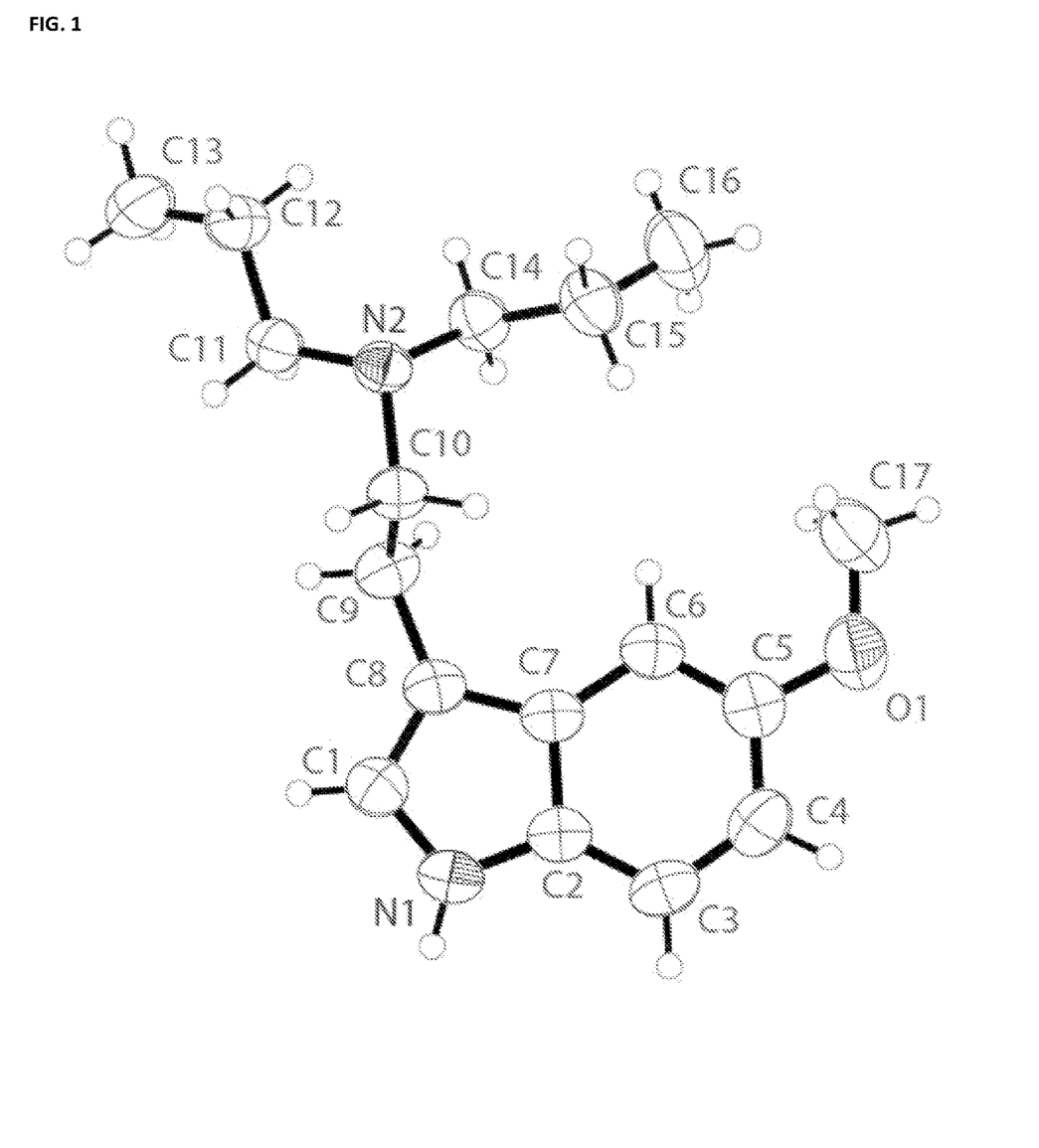
FIG. 1 shows the molecular structure of crystalline form 1 of 5-MeO-DPT, showing the atom labeling.

The molecular structure of crystalline form 1 of 5-MeO-DPT, showing the atom labeling, is shown in FIG. 1.

The molecules are held together by an N1-H1N2 hydrogen bond between the indole N—H and the amino nitrogen atom. The hydrogen bonds join the molecules together in infinite chain along [010].

With regard to the structure, crystalline form 1 of 5-MeO-DPT has a near planar indole unit with a deviation from planarity of 0.012 Å. The methoxy group is in the same plane as the indole ring with a C6-C5-O1-C17 torsion angle of 1.2 (2)°. The ethyl-amino arm is turned away from the indole plane with a C1-C8-C9-C10 torsion angle of 110.4 (2)°.

Figure 2:
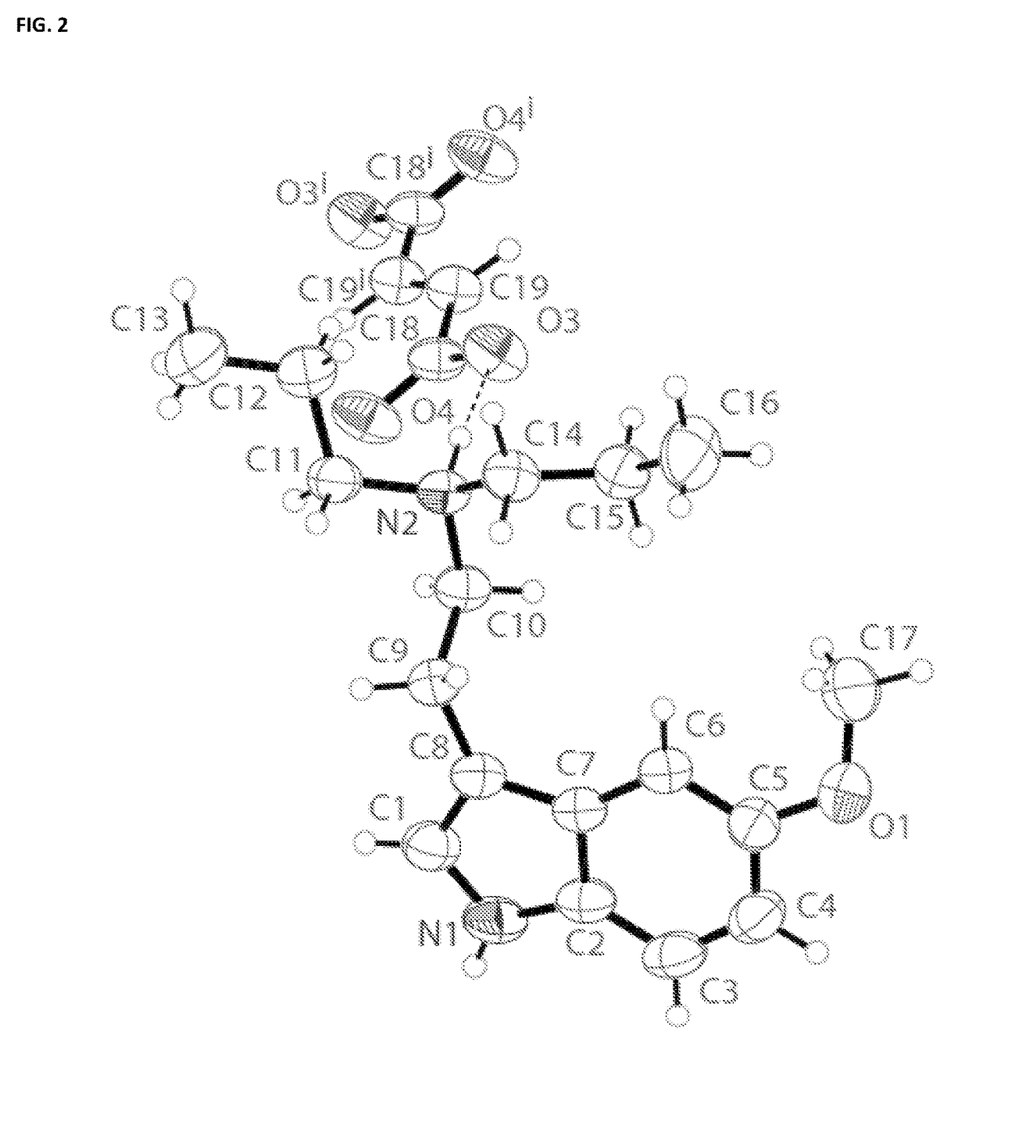
FIG. 2 shows the molecular structure of crystalline form 1 of 5-MeO-DPT fumarate, showing the atom labelling.

The molecular structure of crystalline form 1 of 5-MeO-DPT fumarate, showing the atom labelling, is shown in FIG. 2.

Figure 3:
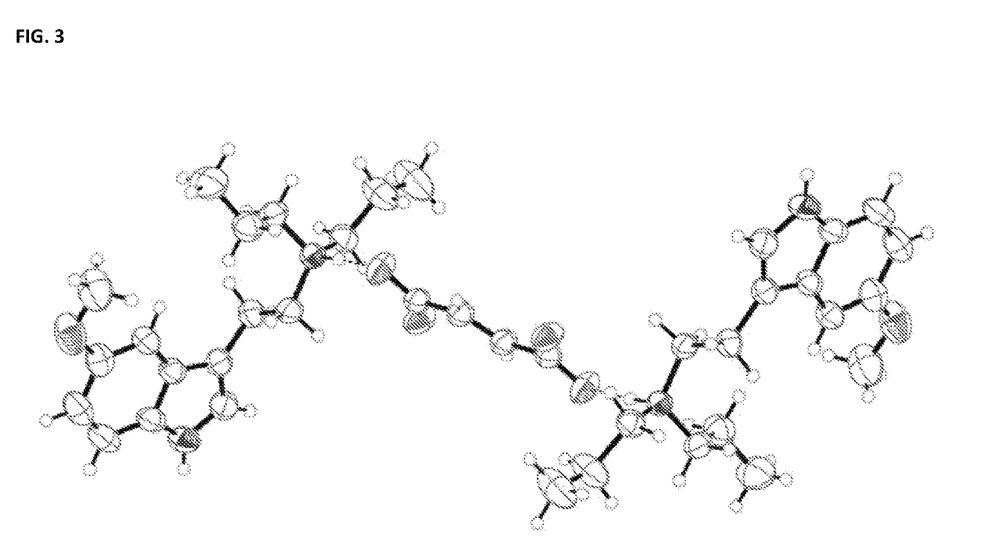
FIG. 3 shows the two to one ratio of 5-MeO-DPT to fumarate crystalline form 1 of 5-MeO-DPT fumarate.

The two to one ratio of 5-MeO-DPT to fumarate in crystalline form 1 of 5-MeO-DPT fumarate as a dimer is shown in FIG. 3.

The tryptammonium cation is linked to the fumarate dianion in the asymmetric unit through an N—H⋯O hydrogen bond between the ammonium nitrogen and a carboxylate of the fumarate. There is also an N—H⋯O hydrogen bond between the indole nitrogen and the other oxygen of the carboxylate group on a symmetry generated fumarate dianion. Two tryptammonium cations and two fumarate dianions are joined together through these hydrogen bonds to form rings with graph-set notation $R^4_4(22)$ (Etter et al., 1990). The rings are joined together by two parallel chains along [001]. These chains have graph-set notation $C^2_2(14)$ and $C^4_4(28)$.

With regard to the structure, crystalline form 1 of 5-MeO-DPT fumarate has a near planar indole unit with a deviation from planarity of 0.015 Å. The methoxy group is turned slightly from the plane of the indole ring with a C6-C5-O1-C17 torsion angle of 13.5 (4)°. The ethyl-amino arm is turned away from the indole plane with a C1-C8-C9-C10 torsion angle of 104.8 (3)°. The fumarate dianion is near planar with a deviation from planarity of 0.022 Å.

Figure 4:
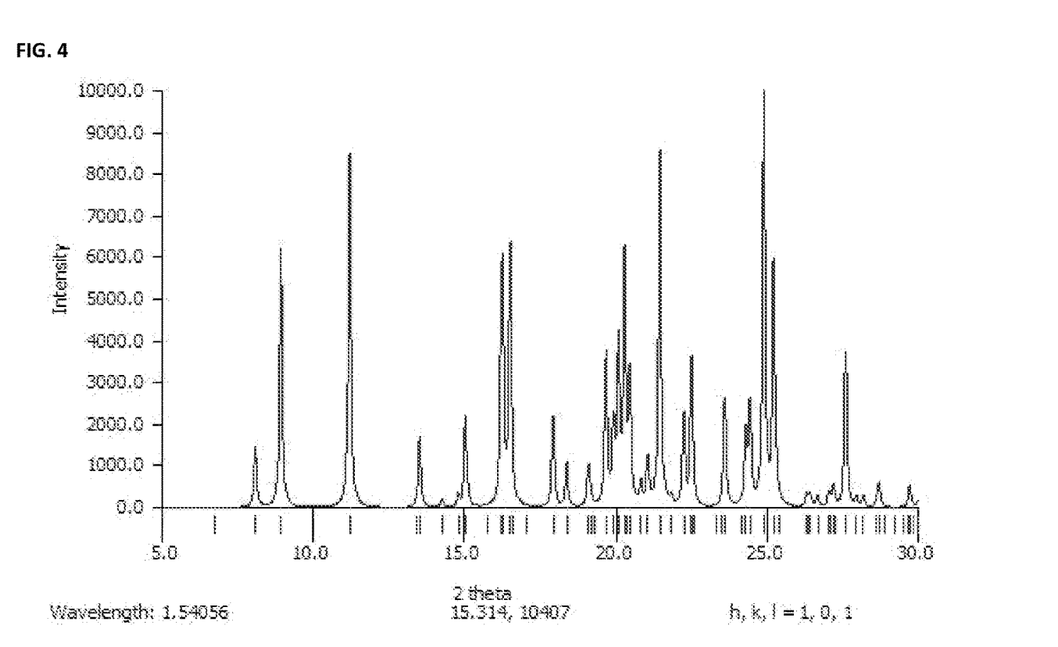
FIG. 4 shows a simulated x-ray powder diffraction (XRPD) of crystalline form 1 of 5-MeO-DPT from its single crystal data.

FIG. 4 is a simulated x-ray powder diffraction (XRPD) of crystalline form 1 of 5-MeO-DPT from its single crystal data. Table 4 lists the angles, °2θ±0.2°2θ, and d-spacing of the peaks identified in the experimental XRPD pattern of FIG. 4. The entire list of peaks, or a subset thereof, may be sufficient to characterize the cocrystal. For example, crystalline form 1 of 5-MeO-DPT may be characterized by at least two peaks selected from the peaks at 8.1, 8.9, and 11.2°2θ±0.2°2θ or their corresponding d-spacing as well as by an XRPD pattern substantially similar to FIG. 4.

TABLE 4

| d-spacing (Å) | 2(Theta deg) | Intensity |
|---|---|---|
| 10.92 | 8.1 | 1404.9 |
| 9.88 | 8.9 | 7231.5 |
| 7.89 | 11.2 | 15799.6 |
| 6.55 | 13.5 | 4633.4 |
| 6.21 | 14.2 | 523.1 |
| 5.99 | 14.8 | 890.4 |
| 5.89 | 15.0 | 7200.5 |
| 5.88 | 15.1 | 30.4 |
| 5.62 | 15.8 | 3.0 |
| 5.46 | 16.2 | 10170.9 |
| 5.45 | 16.3 | 16059.9 |
| 5.36 | 16.5 | 25222.9 |
| 4.95 | 17.9 | 3014 |
| 4.94 | 17.9 | 7781.8 |
| 4.82 | 18.4 | 5368.3 |
| 4.64 | 19.1 | 5147.0 |
| 4.62 | 19.2 | 958.9 |
| 4.60 | 19.3 | 9.2 |
| 4.51 | 19.7 | 21214.9 |
| 4.45 | 19.9 | 10782.7 |
| 4.42 | 20.1 | 22629.7 |
| 4.37 | 20.3 | 36426.6 |
| 4.34 | 20.5 | 18672.6 |
| 4.26 | 20.8 | 3331.9 |
| 4.22 | 21.1 | 7329.3 |
| 4.14 | 21.5 | 59740 |

TABLE 4-continued

| d-spacing (Å) | 2(Theta deg) | Intensity |
|---|---|---|
| 4.07 | 21.8 | 1429.1 |
| 3.99 | 22.2 | 16697.6 |
| 3.94 | 22.5 | 27357.7 |
| 3.79 | 23.5 | 86.7 |
| 3.76 | 23.6 | 22076.1 |
| 3.76 | 23.6 | 471.1 |
| 3.68 | 24.2 | 91.3 |
| 3.66 | 24.3 | 15557.3 |
| 3.64 | 24.4 | 21237.7 |
| 3.57 | 24.9 | 93286.8 |
| 3.53 | 25.2 | 57884 |
| 3.50 | 25.4 | 15.4 |
| 3.39 | 26.3 | 2212.9 |
| 3.38 | 26.3 | 439.9 |
| 3.38 | 26.3 | 880.1 |
| 3.37 | 26.4 | 3198.1 |
| 3.34 | 26.7 | 2884.5 |
| 3.29 | 27.0 | 1532.7 |
| 3.29 | 27.0 | 2106.7 |
| 3.29 | 27.1 | 84.4 |
| 3.28 | 27.2 | 4365.8 |
| 3.27 | 27.2 | 1164.7 |
| 3.27 | 27.2 | 652.1 |
| 3.23 | 27.6 | 43527.6 |
| 3.20 | 27.9 | 85.0 |
| 3.19 | 27.9 | 2649.3 |
| 3.16 | 28.2 | 2909.1 |
| 3.12 | 28.6 | 1399.3 |
| 3.11 | 28.7 | 2688.1 |
| 3.11 | 28.7 | 4701.9 |
| 3.03 | 29.5 | 332.0 |
| 3.01 | 29.7 | 814.6 |
| 3.00 | 29.7 | 6589.0 |
| 2.99 | 29.8 | 377.9 |
| 2.98 | 30.0 | 1909.6 |

Figure 5:
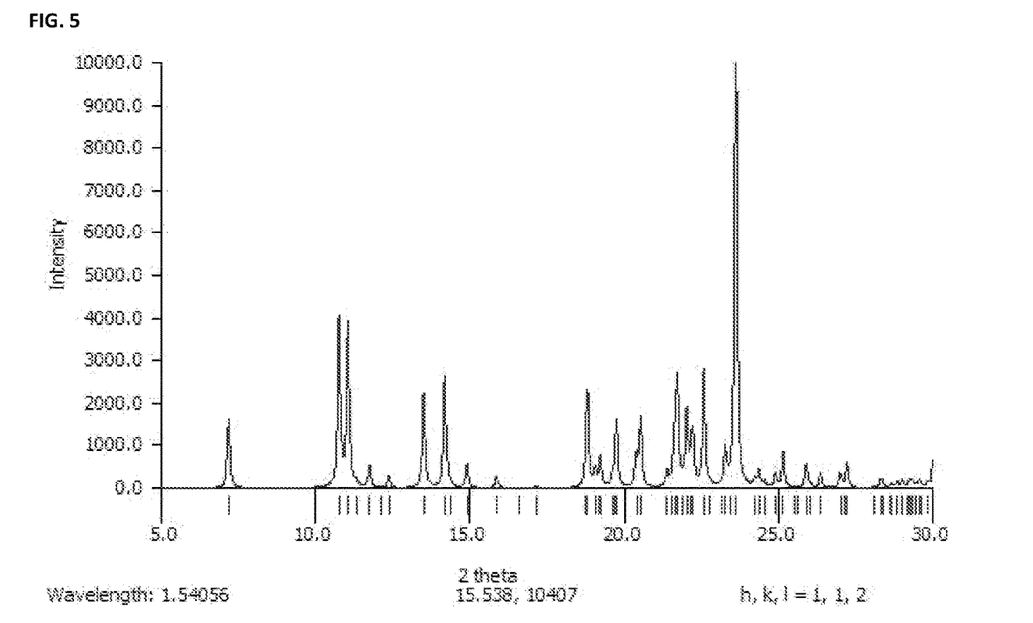
FIG. 5 shows a simulated x-ray powder diffraction (XRPD) of crystalline form 1 of 5-MeO-DPT fumarate from its single crystal data.

FIG. 5 is a simulated x-ray powder diffraction (XRPD) of crystalline form 1 of 5-MeO-DPT fumarate from its single crystal data. Table 5 lists the angles, °2θ±0.2°2θ, and d-spacing of the peaks identified in the experimental XRPD pattern of FIG. 5. The entire list of peaks, or a subset thereof, may be sufficient to characterize the cocrystal. For example, crystalline form 1 of 5-MeO-DPT fumarate may be characterized by at least two peaks selected from the peaks at 7.2, 13.5, and 14.2°2θ±0.2°2θ or their corresponding d-spacing as well as by an XRPD pattern substantially similar to FIG. 5.

TABLE 5

| d-spacing (Å) | 2(Theta deg) | Intensity |
|---|---|---|
| 12.31 | 7.2 | 872.1 |
| 8.21 | 10.8 | 4925.9 |
| 8.00 | 11.1 | 4890.6 |
| 7.81 | 11.3 | 128.3 |
| 7.53 | 11.7 | 760.8 |
| 7.30 | 12.1 | 2.1 |
| 7.15 | 12.4 | 463.5 |
| 6.55 | 13.5 | 4349.3 |
| 6.23 | 14.2 | 5622.7 |
| 6.15 | 14.4 | 65.0 |
| 5.94 | 14.9 | 1298.4 |
| 5.58 | 15.9 | 811.8 |
| 5.34 | 16.6 | 9.0 |
| 5.16 | 17.2 | 186.1 |
| 4.74 | 18.7 | 320.5 |
| 4.71 | 18.8 | 8703.2 |
| 4.65 | 19.1 | 1616.6 |
| 4.62 | 19.2 | 35.3 |
| 4.61 | 19.2 | 2793.3 |
| 4.52 | 19.6 | 1002.8 |
| 4.51 | 19.7 | 0.2 |
| 4.49 | 19.8 | 6734.4 |
| 4.35 | 20.4 | 3175.0 |
| 4.32 | 20.5 | 7422.2 |
| 4.15 | 21.4 | 1667.9 |
| 4.12 | 21.5 | 24.5 |
| 4.10 | 21.6 | 5444.7 |
| 4.10 | 21.6 | 500.4 |
| 4.09 | 21.7 | 11964.2 |
| 4.06 | 21.9 | 474.0 |
| 4.03 | 22.0 | 9006.0 |
| 4.01 | 22.2 | 559.3 |
| 4.01 | 22.2 | 1433.4 |
| 4.00 | 22.2 | 6132.5 |
| 3.93 | 22.6 | 792.4 |
| 3.93 | 22.6 | 14579.2 |
| 3.90 | 22.8 | 264.8 |
| 3.84 | 23.1 | 64.2 |
| 3.82 | 23.3 | 4690.3 |
| 3.79 | 23.5 | 342.0 |
| 3.76 | 23.6 | 60486.4 |
| 3.67 | 24.2 | 1264.8 |
| 3.65 | 24.4 | 2408.3 |
| 3.62 | 24.5 | 784.5 |
| 3.57 | 24.9 | 2262.8 |
| 3.54 | 25.1 | 5941.4 |
| 3.49 | 25.5 | 194.6 |
| 3.47 | 25.6 | 46.3 |
| 3.44 | 25.9 | 4090.3 |
| 3.42 | 26.0 | 476.8 |
| 3.38 | 26.4 | 2623.9 |
| 3.30 | 27.0 | 2542.5 |
| 3.28 | 27.2 | 122.0 |
| 3.27 | 27.2 | 103.0 |
| 3.27 | 27.2 | 4526.0 |
| 3.18 | 28.1 | 78.9 |
| 3.15 | 28.3 | 1379.5 |
| 3.14 | 28.4 | 1133.0 |
| 3.12 | 28.6 | 246.2 |
| 3.11 | 28.7 | 708.5 |
| 3.09 | 28.8 | 1386.5 |
| 3.08 | 29.0 | 1.7 |
| 3.08 | 29.0 | 254.2 |
| 3.08 | 29.0 | 1330.6 |
| 3.06 | 29.2 | 707.8 |
| 3.06 | 29.2 | 20.3 |
| 3.05 | 29.2 | 491.6 |
| 3.05 | 29.3 | 157.4 |
| 3.05 | 29.3 | 691.1 |
| 3.04 | 29.3 | 1158.5 |
| 3.03 | 29.4 | 297.8 |
| 3.02 | 29.5 | 1413.7 |
| 3.01 | 29.6 | 585.9 |
| 2.99 | 29.8 | 1293.3 |

REFERENCES

Bruker (2018). APEX3, SAINT, and SADABS. Bruker AXS Inc., Madison, Wisconsin, USA.

Carhart-Harris, R. L. & Goodwin, G. M. (2017). Neuropsychopharmacology, 42, 2105-2113.

Chadeayne, A. R., Golen, J. A. & Manke, D. R. (2019a). Acta Cryst. E75, 900-902.

Chadeayne, A. R., Golen, J. A. & Manke, D. R. (2019b). IUCrData, 4, x190962.

Chadeayne, A. R., Golen, J. A. & Manke, D. R. (2019c). Psychedel. Sci. Rev. https://psychedelicreview.com/the-crystal-structure-of-4-aco-dmt-fumarate/.

Chadeayne, A. R., Pham, D. N. K., Golen, J. A. & Manke, D. R. (2019). Acta Cryst. E75, 1316-1320.

Dolomanov, O. V., Bourhis, L. J., Gildea, R. J., Howard, J. A. K. & Puschmann, H. (2009). J. Appl. Cryst. 42, 339-341.

Etter, M. C., MacDonald, J. C. & Bernstein, J. (1990). Acta Cryst. B46, 256-262.

Falkenberg, G. (1972). Acta Cryst. B28, 3075-3083.
Petcher, T. J. & Weber, H. P. (1974). J. Chem. Soc. Perkin Trans. 2, pp. 946-948.
Sheldrick, G. M. (2015a). Acta Cryst. A71, 3-8.
Sheldrick, G. M. (2015b). Acta Cryst. C71, 3-8.
Weber, H. P. & Petcher, T. J. (1974). J. Chem. Soc. Perkin Trans. 2, pp. 942-946.
Westrip, S. P. (2010). J. Appl. Cryst. 43, 920-925.

The claimed invention is:

1. Crystalline form 1 of [2-(5-methoxy-1H-indol-3-yl)ethyl]dipropylamine (5-MeO-DPT).

2. Crystalline form 1 of 5-MeO-DPT according to claim 1 characterized by at least one of:
a monoclinic, $P2_1/n$ crystal system space group at a temperature of about 297 K;
unit cell dimensions a=6.2223 (3) Å, b=13.0931 (6) Å, c=19.7791 (10) Å, and β=91.825 (2)°;
an X-ray powder diffraction pattern characterized by at least two peaks selected from 8.1, 8.9, and 11.2°2θ+ 0.2°2θ; or
an X-ray powder diffraction pattern substantially similar to FIG. 4.

3. A composition comprising crystalline form 1 of 5-MeO-DPT according to claim 1 and an excipient.

4. A pharmaceutical composition comprising a therapeutically effective amount of crystalline form 1 of 5-MeO-DPT according to claim 1 and a pharmaceutically acceptable excipient.

5. A composition comprising crystalline form 1 of 5-MeO-DPT according to claim 1 and a second component selected from (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

6. A method of treating a psychological disorder comprising the steps of:
identifying a subject in need of treatment; and
administering to the subject in need thereof a therapeutically effective amount of crystalline form 1 of 5-MeO-DPT according to claim 1,
wherein the psychological disorder is selected from the group consisting of depression, anxiety, and post-traumatic stress disorder (PTSD).

7. A method of treating pain comprising the steps of:
identifying a subject in need of treatment; and
administering to the subject in need thereof a therapeutically effective amount of crystalline form 1 of 5-MeO-DPT according to claim 1.

8. A method of promoting neurogenesis, comprising administering a neurogenesis modulator composition comprising crystalline form 1 of 5-MeO-DPT according to claim 1.

9. A method of promoting neurite outgrowth, comprising administering a composition comprising crystalline form 1 of 5-MeO-DPT according to claim 1.

10. Crystalline form 1 of bis([2-(5-methoxy-1H-indol-3-yl)ethyl]dipropylazanium) (2E)-but-2-enedioate (5-MeO-DPT fumarate).

11. Crystalline form 1 of 5-MeO-DPT fumarate according to claim 10 characterized by at least one of:
a triclinic, P"1 crystal system space group at a temperature of about 297 K;
unit cell dimensions a=9.2956 (6) Å, b=9.4443 (6) Å, c=12.7427 (8) Å, α=78.552 (2)°, β=75.929 (2)°, and γ=60.806 (2)°;
an X-ray powder diffraction pattern characterized by at least two peaks selected from 7.2, 13.5, and 14.2°2θ+ 0.2°2θ; or
an X-ray powder diffraction pattern substantially similar to FIG. 5.

12. A composition comprising crystalline form 1 of 5-MeO-DPT fumarate according to claim 10 and an excipient.

13. A pharmaceutical composition comprising a therapeutically effective amount of crystalline form 1 of 5-MeO-DPT fumarate according to claim 10 and a pharmaceutically acceptable excipient.

14. A composition comprising crystalline form 1 of 5-MeO-DPT fumarate according to claim 10 and a second component selected from (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

15. A method of treating a psychological disorder comprising the steps of:
identifying a subject in need of treatment; and
administering to the subject in need thereof a therapeutically effective amount of crystalline form 1 of 5-MeO-DPT fumarate according to claim 10,
wherein the psychological disorder is selected from the group consisting of depression, anxiety, and post-traumatic stress disorder (PTSD).

16. A method of treating pain comprising the steps of:
identifying a subject in need of treatment; and
administering to the subject in need thereof a therapeutically effective amount of crystalline form 1 of 5-MeO-DPT fumarate according to claim 10.

17. A method of promoting neurogenesis, comprising administering a neurogenesis modulator composition comprising crystalline form 1 of 5-MeO-DPT fumarate according to claim 10.

18. A method of promoting neurite outgrowth, comprising administering a composition comprising crystalline form 1 of 5-MeO-DPT fumarate according to claim 10.

* * * * *